(12) United States Patent
Clarke

(10) Patent No.: US 9,581,535 B2
(45) Date of Patent: Feb. 28, 2017

(54) MEASUREMENT OF INTERFACIAL PROPERTY

(71) Applicant: SCHLUMBERGER TECHNOLOGY CORPORATION, Sugar Land, TX (US)

(72) Inventor: Andrew Clarke, Haslingfield (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 583 days.

(21) Appl. No.: 13/892,994

(22) Filed: May 13, 2013

(65) Prior Publication Data

US 2013/0298649 A1 Nov. 14, 2013

(30) Foreign Application Priority Data

May 14, 2012 (GB) .................................... 1208366.3

(51) Int. Cl.
*G01N 13/00* (2006.01)
*G01N 13/02* (2006.01)

(52) U.S. Cl.
CPC .................... *G01N 13/02* (2013.01)

(58) Field of Classification Search
CPC ................ G01N 13/02; B01L 2400/00; B01L 2400/0415; B01L 2400/0418;

(Continued)

(56) References Cited

U.S. PATENT DOCUMENTS 4,196,615 A    4/1980   Davis
4,391,129 A *  7/1983   Trinh et al. .................. 73/64.48
               (Continued)

FOREIGN PATENT DOCUMENTS

DE    2915956     11/1980
EP    149500      7/1985
               (Continued)

OTHER PUBLICATIONS

Ren, H, R. Fair and M. Pollack. Automated on-chip droplet dispensing with volume control by electro-wetting actuation and capacitance metering. Sensors and Actuators. 2004. pp. 319-327.*

(Continued)

*Primary Examiner* — John Fitzgerald
*Assistant Examiner* — Tarun Sinha

(57) ABSTRACT

Interfacial tension between first and second immiscible liquids is determined using a device in which entrance and exit channels are connected by a cavity with wider cross-section. A flow of the first liquid enters the cavity as a jet and breaks into droplets within the cavity. Passage of a droplet through the exit channel feeds back to perturb the jet entering the cavity. An alternating signal applied to a heating element perturbs the incoming jet and is progressively scanned over a frequency range which includes the system's resonant frequency (frequency of droplet formation with no signal to the heating element). A bandwidth of frequency is observed in which the frequency of droplet formation is phase locked to the frequency applied to the heater. The ratio of resonant frequency to this bandwidth is a measurement of the interfacial tension between the two liquids.

9 Claims, 1 Drawing Sheet

(58) Field of Classification Search
CPC ..... B01L 2400/0421; B01L 2400/0424; B01L 2400/0427; B01L 2400/043; B01L 2400/0433; B01L 2400/0436; B01L 2400/0439
USPC .................................. 73/64.52, 64.48, 64.53
See application file for complete search history.

(56) References Cited

U.S. PATENT DOCUMENTS

| | | | |
|---|---|---|---|
| 5,394,740 | A | 3/1995 | Schramm et al. |
| 5,542,289 | A | 8/1996 | Hool et al. |
| 8,613,217 | B2 | 12/2013 | Colin et al. |
| 2004/0144175 | A1* | 7/2004 | Sinha ..................... G01N 13/02 73/579 |
| 2009/0019924 | A1* | 1/2009 | Nguyen et al. ............. 73/64.52 |
| 2010/0017135 | A1 | 1/2010 | Mostowfi |
| 2010/0170957 | A1* | 7/2010 | Clarke ............................. 239/1 |
| 2011/0197664 | A1 | 8/2011 | Colin et al. |
| 2013/0293246 | A1* | 11/2013 | Pollack ............. B01L 3/502784 324/671 |

FOREIGN PATENT DOCUMENTS

| | | |
|---|---|---|
| GB | 2502058 | 11/2013 |
| WO | 2009004314 A1 | 1/2009 |
| WO | 2009125119 A1 | 10/2009 |
| WO | 2013090690 | 6/2013 |

OTHER PUBLICATIONS

Combined Search and Examination Report of British Application No. GB1307185.7 dated Sep. 3, 2013: pp. 1-7.
Gu et al., "Interfacial tension measurements with microfluidic tapered channels," Colloids and Surfaces A: Physicochemical and Engineering Aspects, 2011, vol. 389: pp. 38-42.
Manning-Benson et al., "Article No. CS974797: Measurement of Dynamic Interfacial Properties in an Overflowing Cylinder by Ellipsometry," Journal of Colloid and Interface Science, 1997, vol. 189: pp. 109-116.
Sherwood, "Potential flow around a deforming bubble in a Venturi," International Journal of Multiphase Flow, 2000, vol. 26: pp. 2005-2047.
Combined Search and Examination Report of British Application No. 1208366.3 dated Aug. 21, 2012: pp. 1-5.

* cited by examiner

MEASUREMENT OF INTERFACIAL PROPERTY

CROSS-REFERENCE TO RELATED APPLICATION

This application claims priority to British Application No. 1208366.3 filed May 14, 2012. which is incorporated herein by reference in its entirety.

BACKGROUND

Interfacial tension is a property of the interface between two immiscible liquid phases and is analogous to surface tension at the interface between a liquid and a gas. It is thus a relative property of two liquids in contact. Interfacial tension can be defined as free energy per unit area of interface. Methods and devices for determining interfacial tension between two immiscible liquids are known. For instance, pendant drop methods, spinning drop methods. These methods are designed to exploit a balance between forces generated by the interface with gravity or centripetal acceleration respectively. Other methods utilize a probe, e.g., a plate or wire, that crosses the interface. In these methods, the force exerted by the interfacial tension on the probe is directly measured using a balance. A microfluidic sensor is disclosed in US20090019924 and another in US20110197664 (previously published in French as WO2009/125119). The latter relies on observation of the flow of one liquid within another and determines interfacial tension between the liquids from the flow rate at which the manner of flow changes from a jet to a stream of droplets. In this case the interfacial tension force is balanced by the viscous force introduced by the flow.

SUMMARY

This summary is provided to introduce a selection of concepts that are further described below. This summary is not intended to be used as an aid in limiting the scope of the subject matter claimed.

Disclosed here is a method of characterizing an interfacial property between first and second immiscible liquids, comprising directing a flow of the first liquid surrounded by a flow of the second liquid into a succession of three channels which comprise an entrance channel, an exit channel and a cavity connecting the entrance and exit channels where this cavity has a wider cross-section for flow than the entrance and exit channels, such that the first liquid passes through the entrance channel and enters the cavity as a jet which breaks into droplets within the cavity and such that passage of a droplet through the exit channel creates a perturbation which feeds back to perturb the jet entering the cavity, supplying an alternating signal to perturb the incoming flow of the first liquid at the frequency of the supplied signal, varying the frequency of the said signal over a range, and determining a bandwidth of signal frequency within which formation of droplets takes place at the frequency of the said signal.

The size of this bandwidth provides a characterization of the interface between the first and second liquids and in some embodiments it provides a measure of interfacial tension. Interfacial tension may be determined, possibly using a calibration made with liquids where the interfacial tension is known.

Apparatus for carrying out the method may comprise an entrance channel and an exit channel which are connected by a cavity which has a wider cross-section for flow than the entrance and exit channels, means for flowing a first liquid surrounded by a flow of a second liquid through the entrance channel into the cavity, a signal generator for supplying an alternating signal, means connected to the signal generator for applying a perturbation to the flow of the first liquid through the entrance channel at the frequency of the said signal, means for detecting whether the frequency of formation of droplets of the first liquid matches the frequency of the said signal, and a controller for varying the frequency of the said signal over a range and determining a bandwidth within which formation of droplets takes place at the frequency of the said signal.

The apparatus may also comprise one or more controllers for varying the flow rates or entry pressures of the first and second liquids.

The means for applying a perturbation to the flow through the entrance channel may for instance be a heating element or a pressure transducer.

The apparatus may have means to detect passage of a droplet, for example a detector for a light beam interrupted or diverted by a droplet passing through it. A light beam may or may not be visible light. The apparatus may have means to measure the frequency of a signal from the detector and compare it with the frequency from the signal generator. In a slightly different alternative, the apparatus has means to determine when a signal from the detector is phase locked with the signal from the signal generator.

DETAILED DESCRIPTION

Figure 1:
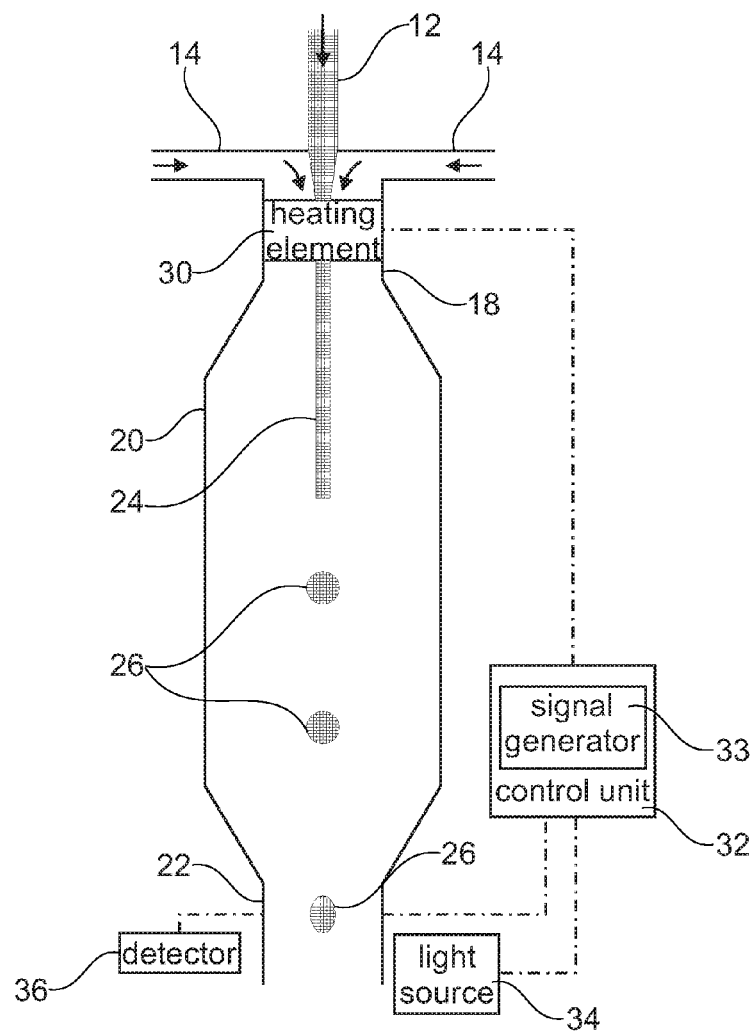
FIG. 1 is a schematic cross-section of a device used in determining interfacial tension.

FIG. 1 shows a microfluidic device used in determining interfacial tension. It has an inlet channel 12 for entry of a first liquid and two inlet channels 14 for the entry of a second liquid. The liquids flow into a succession of three channels which begin with an entrance channel 18. Here the liquids flow as a stream of the first liquid surrounded by an annular stream of the second liquid. The entrance channel 18 leads into a cavity 20 of wider cross-section which in turn leads to an exit channel 22 with a narrower cross section than the cavity 20. The cross-sections of the entrance and exit channels 18, 20 do not need to be the same, but in some embodiments the exit channel 22 is approximately the same as the cross-section of the entrance channel 18. The first liquid enters the cavity 20 from the entrance channel 18 as a jet 24 which breaks up into droplets 26.

The device has microfluidic dimensions such that the entrance channel 18 and exit channel 22 are capillaries less than 1 mm in internal width.

A device having this general configuration is described in WO2009/004314 also published as US20100170957 (the disclosure of which is incorporated herein by reference) where it is used to generate droplets of uniform size.

The apparatus dimensions and the flow rates of the liquids are arranged such that droplets 26 of the first liquid passing through the exit channel 22 occupy a substantial proportion of the available cross-section of the exit channel 22, for example at least one third of its cross-section. In these circumstances each droplet passing through the exit channel 22 creates a perturbation of the flow regime in the wider cavity 20 and perturbs the jet 24 entering the cavity 20. This feed-back stabilizes the frequency at which droplets 26 are formed from the jet 24. Consequently the droplet frequency can remain precisely constant so long as the geometry of the device and the properties and flow rates of the liquids remain unchanged.

This behaviour is a form of resonance and WO2009/004314 describes observing droplets in the exit channel by stroboscopic illumination at the frequency of droplet formation. This frequency stabilised by feedback from droplets passing through the exit channel will be referred to as the "resonant frequency" of the device.

A device 30 to perturb the flow of the outer fluid is placed either on the entrance channel 18 or on the entrance channel 14, or on a combination of channels 14 and 18. An example of such a device is a heater element formed as a thin layer of conductive material is deposited as a narrow zigzag strip on the inside wall of entrance channel 18 to form a small electrically resistive heating element 30. This may be provided using materials and dimensions as described in WO2009/004314 which provided a resistance of around 350 ohms. A control unit 32 which includes an alternating signal generator 33 is electrically connected to the heating element 30 so that the signal can be applied to the heating element 30. The alternating signal from the signal generator 33 may be a square wave or may be a pulse sequence or any other signal suitable to drive the device 30. For a resistive heating element, this signal causes heating of the heating element 30 at the signal frequency, and this in turn perturbs the jet 24 at the signal frequency as the jet 24 enters the cavity 20.

When the applied electrical signal is at the resonant frequency, the perturbations caused by operation of the heating element 30 and the perturbations which are feedback from the exit channel 22 maintain an unchanging phase relationship to each other. Droplet formation and the frequency of passage of droplets through the channel 22 are phase locked to the electrical signal from the signal generator 33.

The device includes provision for detecting droplets that form in the cavity 20 and ultimately pass through the exit channel 22. The droplet detecting device can be placed at any point subsequent to the breakup of the liquid jet and so it may detect droplets before, during or after their passage through the exit channel 22. As shown in this embodiment, a light source 34 which may be a laser directs a beam towards a detector 36 which may be a fast photodiode. The light source 34 may direct a continuous beam of light (which may or may not be visible light) towards the detector 36 which is able to detect interruption of the light beam by droplets. The frequency of droplet formation will then be the frequency of interruptions which can be determined from the output of the detector 36. This is done by circuitry in the control unit 32 which also compares the output frequency from the detector 36 with the frequency from the signal generator 33 to detect when they are the same. Additionally, by using the detector 36 to detect the time for which the light beam is interrupted by a droplet and taking overall flow rate into account, the droplet size can also be measured.

For determining interfacial tension, the device may initially be run with no signal from the signal generator applied to the heating element 30. Droplet formation will take place at the resonant frequency which is measured by the control unit 32 using the output from detector 36. Then a signal from the signal generator 33 is applied to the heating element 30. The control unit 32 progressively scans the frequency of the alternating electrical signal from the signal generator 33 over a range which extends across the resonant frequency of the device. If the applied electrical signal is at a frequency which is slightly different from the resonant frequency of the device, the application of the electrical signal from the signal generator 33 to the heater 30 will cause the device to produce droplets at the frequency of this signal, even though this is slightly different from the resonant frequency. The frequency of droplet formation remains phase locked to the frequency of the applied electric signal. However, as the frequency difference between the signal applied to the heater 30 and the resonant frequency increases, a point is reached at which the observed frequency of droplet formation ceases to be the same as the frequency of the signal from the generator 33 applied to heater 30. Furthermore there ceases to be a constant phase relation between the heater signal and the detector signal. There is thus a limited bandwidth of signal frequency extending to either side of the resonant frequency, at which the frequency of droplet formation is phase locked with the signal from the generator 33 applied to the heater 30. This bandwidth is determined by the detector 36 and control unit 32 as the signal from the generator 33 is scanned across a range of frequencies. The inventor has recognized that determining this bandwidth provides a measure of the interfacial tension between the liquids.

The measured bandwidth will depend on drop size (which in turn depends on first and second liquid relative flow rates), exit orifice size, viscosity of each liquid, and interfacial properties (interfacial tension and interfacial elasticity). The drop size may be determined either by initial calibration from relative flow rates or by direct in-situ measurement from the sensor 36. The exit orifice is defined by the design and is thus a known parameter. The viscosity (rheology) of each liquid may be measured separately of may be inferred from a measurement of the pressure drop along channels 12 and 14 respectively, i.e., the single phase flow lines. Such a deduction is well known in the art.

If the resonant frequency is denoted as $f$ and $\Delta f$ denotes the bandwidth frequencies within which the frequency of droplet formation is phase locked to the frequency of the signal applied to the heater 30, then the dimensionless ratio $f/\Delta f$ is the quality factor Q of the resonant system.

Figure 2:
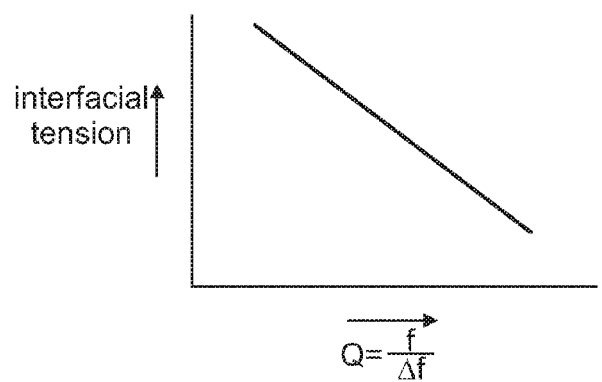
FIG. 2 shows the general form of a plot of interfacial tension against observed bandwidth.

This ratio Q is determined by a number of properties of the system including geometry of the cavity, but if geometry of the system, the flow rates and temperature do not change, Q is inversely related to the interfacial tension of the two liquids. A graph of interfacial tension against Q with interfacial tension on the vertical axis and $Q=f/\Delta f$ as determined from measured data along the horizontal axis will have the form shown by FIG. 2. The graph will have similar form if the horizontal axis shows the frequency bandwidth over which droplet frequency remains phase locked to applied electrical signal frequency.

To obtain determinations of interfacial tension the device may be calibrated, using known liquids to provide pairs of liquids with known interfacial tension. Measurements of bandwidth for these known liquids are carried out while keeping droplet size constant by adjustment of liquid flow rates and also keeping temperature constant. These measurements provide a calibration plot, similar to that schematically shown in FIG. 2 and this can then be used to derive a value of interfacial tension from a measurement of bandwidth for a pair of liquids where the interfacial tension is unknown.

The device may also be utilized to check whether the bandwidth observed for one liquid within another falls within a previously chosen range of values or lies above or below a chosen boundary value. This could be done as a quality check or as part of a process control procedure.

Some variations in the construction of the device are possible. A pressure transducer could be used in place of heater 30 as a way to perturb the jet 24 at a controllable frequency. Droplets which form in the cavity 20 and ultimately pass through the exit channel could be detected with a capacitive sensor rather than with a light beam.

To determine when droplet formation is phase locked at the frequency of the signal from the generator 33, the control unit 32 may test whether the output signal from the detector 36 maintains a constant phase relation to the signal from the generator 33. Alternatively, stroboscopic illumination could be employed as mentioned in WO2009/004314. For this, the light source 34 may be made to flash at the frequency of the signal from the generator 33 and the control unit 32 may be configured to check whether the output signal from detector 36 is a uniform signal. It is also possible that the control unit 32 would provide a display of the output signal from the detector and a human operator would make a judgment of when it became uniform, as exemplified by use of a video camera in WO2009/004314.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:

1. A method of determining interfacial tension between first and second immiscible liquids, comprising
   directing a flow of the first liquid surrounded by a flow of the second liquid into a succession of three channels comprising an entrance channel, a cavity and exit channel, where the cavity connects the entrance and exit channels and has a wider cross-section for flow than both the entrance and exit channels,
   wherein the first liquid enters the cavity as a jet and breaks into droplets within the cavity, and
   wherein passage of a droplet through the exit channel creates a perturbation which feeds back to perturb the jet entering the cavity, whereby droplets can be formed within the cavity at a stable resonant frequency;
   supplying an alternating signal to perturb the incoming jet of the first liquid at the frequency of the supplied alternating signal; and
   varying the frequency of the supplied alternating signal over a range which includes the resonant frequency;
   observing the frequency of droplet formation while varying the frequency of the supplied alternating signal, so as to determine a frequency bandwidth which extends to either side of the resonant frequency and within which formation of droplets takes place at the frequency of the supplied alternating signal;
   also directing the flows of first and second liquids through the channels without the said alternating signal so as to determine the resonant frequency of droplet formation without the alternating signal; and
   determining a ratio of the resonant frequency to the bandwidth as a measurement of interfacial tension between the first and second liquids.

2. A method according to claim 1 which includes directing the flows of first and second liquids through the channels without the said alternating signal;
   measuring the size of droplets; and
   determining a frequency bandwidth within which formation of droplets takes place.

3. A method according to claim 1 further comprising a determination of the drop size.

4. A method according to claim 1 further comprising a determination of the rheological properties of the said first and second liquids.

5. A method according to claim 1, further comprising carrying out the steps of the method with combinations of liquids of known interfacial tension so as to establish a relation between interfacial tension and bandwidth.

6. A method according to claim 1, wherein the bandwidth is the bandwidth within which formation of droplets takes place at a frequency which is phase locked to the frequency of the supplied alternating signal.

7. A method of determining interfacial tension between first and second immiscible liquids, comprising
   providing a succession of three flow channels in which an entrance channel and an exit channel are connected by a cavity which has a wider cross-section for flow than both the entrance and exit channels, a signal generator for supplying an alternating perturbation at the frequency of the supplied signal at the entrance channel; and a controller for varying the frequency of the supplied signal over a range;
   directing a flow of the first liquid surrounded by a flow of the second liquid into the entrance channel, from where the first liquid enters the cavity as a jet and breaks into droplets within the cavity, and passage of a droplet through the exit channel creates a perturbation which feeds back to perturb the jet entering the cavity, whereby droplets can be formed within the cavity at a stable resonant frequency;
   observing the resonant frequency of droplet formation while there is no signal from the signal generator;
   supplying an alternating signal to perturb the incoming jet of the first liquid at the frequency of the supplied alternating signal;
   varying the frequency of the supplied alternating signal over a range which includes the resonant frequency; and
   observing the frequency of droplet formation while varying the frequency of the supplied alternating signal, so as to determine a frequency bandwidth which extends to either side of the resonant frequency and within which formation of droplets takes place at the frequency of the supplied alternating signal; and
   determining a ratio of the resonant frequency to the bandwidth as a measurement of interfacial tension between the first and second liquids.

8. A method according to claim 7 wherein supplying an alternating signal to perturb the incoming jet of the first liquid comprises supplying the alternating signal to a heating element at the entrance channel.

9. Apparatus according to claim 7 wherein observing passage of droplets is carried out with a light source directing a beam across the exit channel to a detector.

* * * * *